United States Patent [19]

Ozaki et al.

[11] Patent Number: 5,466,705
[45] Date of Patent: Nov. 14, 1995

[54] TRIAZOLE DERIVATIVES PEST CONTROLLING AGENT AND PEST CONTROL METHOD

[75] Inventors: Masami Ozaki; Atsuhiko Ikeda; Takashi Yumita; Reijiro Honami; Naokazu Minoguchi; Hiroyuki Yano; Norihiko Izawa, all of Shizuoka; Tadayoshi Hirano, Kakegawa, all of Japan

[73] Assignees: Kumiai Chemical Industry Co., Ltd.; Ihara Chemical Industry Co., Ltd., both of Tokyo, Japan

[21] Appl. No.: 182,091

[22] PCT Filed: Jul. 22, 1993

[86] PCT No.: PCT/JP93/01022

§ 371 Date: Jan. 21, 1994

§ 102(e) Date: Jan. 21, 1994

[87] PCT Pub. No.: WO94/02471

PCT Pub. Date: Feb. 3, 1994

[30] Foreign Application Priority Data

| Jul. 24, 1992 | [JP] | Japan | 4-198618 |
| Jul. 24, 1992 | [JP] | Japan | 4-198619 |
| Jul. 31, 1992 | [JP] | Japan | 4-223651 |

[51] Int. Cl.$^6$ .............. A01N 43/653; C07D 249/08
[52] U.S. Cl. .......... 514/383; 548/262.2; 548/267.2; 548/267.4; 548/267.8; 548/268.6; 548/269.4
[58] Field of Search .............. 514/383; 548/262.2, 548/267.2, 267.4, 267.8, 268.6, 269.4

[56] References Cited

U.S. PATENT DOCUMENTS

| 4,119,635 | 10/1978 | Omodei-Sale et al. | 514/383 |
| 4,151,169 | 4/1979 | Sale et al. | 514/383 |
| 4,414,221 | 11/1983 | Parsons et al. | 514/383 |
| 4,788,210 | 11/1988 | Luthy et al. | 514/383 |

OTHER PUBLICATIONS

Research Disclosure vol. 278, Jun. 1987, pp. 356–357, "New 1–Methyl–1H–1,2,4–triazoles".

Heteroocycles, vol. 36, No. 3, Mar. 1993, M. M. El–Abadelah et al pp. 455–472 "Ring Transformations of Heterocycles".

Regioselective Synthesis of 1,2,4–Triazole and 1,2, 4–Oxadiazole Derivatives, Miguel A. Perez, et al, Synthesis, pp. 483–486, 1983.

Primary Examiner—Patricia L. Morris
Attorney, Agent, or Firm—Stevens, Davis, Miller & Mosher

[57] ABSTRACT

There are provided triazole derivatives represented by a general formula

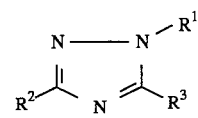

(wherein $R^1$ is an alkyl group having a carbon number of 1-4, $R^2$ is a phenyl group substitutable with a halogen atom, an alkyl group having a carbon number of 1–4 or the like, $R^3$ is an alkenyl group having a carbon number of 3 or more substitutable with 1–4 halogen atoms, a phenyl group substituted with 1 or more halogen atoms or the like), a method producing the same, and a pest controlling agent containing the same as an active ingredient.

The triazole derivatives according to the invention have an excellent insecticidal action against harmful pests such as hemipteran insects, lepidopteran insects, dipteran insects, mites and the like and also have an excellent ovicidal action against eggs of these pests. Furthermore, they have a preventively controlling effect on serious diseases such as sheath blight, blast and the like without badly affecting crops.

4 Claims, No Drawings

TRIAZOLE DERIVATIVES PEST CONTROLLING AGENT AND PEST CONTROL METHOD

TECHNICAL FIELD

This invention relates to triazole derivatives, method of producing the same, pest controlling agent and pest control method. More particularly, it relates to insecticide, acaricide and fungicide and methods thereof.

BACKGROUND ART

Recently, in the control of pests and the like harming paddy rice and garden crops, plant-parasitic pests and mites reveal the resistance to existing chemicals by continuous application of the same chemical, so that the remarkable decrease of control effect becomes a serious problem. Therefore, it is demanded to develop chemicals of new type having insecticidal and acaricidal mechanisms and different usages.

Up to the present, there are known 3-(o-chlorophenyl)-5-cyclohexyl-1-methyl-1H-1,2,4-triazole and the like as an insecticide and acaricide (specification of U.S. Pat. No. 4,414,221). However, the compounds concretely disclosed in this patent specification are insufficient in the insecticidal and acaricidal activities. Moreover, there is no description on the activity against pests harming paddy rice such as brown planthopper, green rice leafhopper and the like.

The inventors have synthesized various triazole derivatives in order to cope with the above situation and made various studies with respect to insecticidal activity thereof and found out that triazole derivatives obtained by introducing a phenyl group substituted with a halogen atom or the like, a cycloalkyl group substitutable with an alkyl group, an alkenyl group substitutable at 5-position with a halogen atom or the like, or a cycloalkyl group substituted with an alkyl group into 3-position of a triazole derivative have a very excellent insecticidal activity against harmful insects, e.g. aphids such as cotton aphid or the like, hoppers such as brown planthopper or the like, leafhoppers such as green rice leafhopper or the like, lepidoptera pests such as diammondback moth or the like; and harmful mites, e.g. mites such as two-spotted spider mite, citrus red mite or the like.

Further, it has been found that triazole derivatives obtained by introducing a β-chloro-1-cycloalkenyl group having a carbon number of 5–15 into 5-position of a triazole derivative exhibit a remarkable effect against sheath blight and blast as a serious disease injury of paddy rice by a preventive treatment and have a very excellent insecticidal activity against harmful insects, e.g. aphids such as cotton aphid or the like; and harmful mites, e.g. mites such as two-spotted spider mite, citrus red mite or the like, and as a result the invention has been accomplished.

DISCLOSURE OF INVENTION

That is, the triazole derivatives according to the invention are represented by a general formula [I]

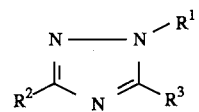

[I]

(wherein $R^1$ is an alkyl group having a carbon number of 1–4, $R^2$ is a phenyl group substitutable with a halogen atom, an alkyl group having a carbon number of 1–4, an alkoxy group, nitro group, a cyano group or a trifluoromethyl group (these substituents in the phenyl group may be 1–5, and a combination thereof may be same or different) or a cycloalkyl group having a carbon number of 3–6 substitutable with an alkyl group having a carbon number of 1–4, R3 is an alkenyl group having a carbon number of 3 or more substitutable with 1–4 halogen atoms, a cycloalkyl group having a carbon number of 3–6 substituted with an alkyl group having a carbon number of 1–4 or a β-chloro-1-cycloalkenyl group having a carbon number of 5–15 (the cycloalkenyl group may be substituted with an alkyl group having a carbon number of 1–4), provided that (a) when $R^2$ is a phenyl group substitutable with 1 or more halogen atoms, an alkyl group having a carbon number of 1–4, an alkoxy group, nitro group, a cyano group or trifluoromethyl group, $R^3$ is an alkenyl group having a carbon number of 3 or more substitutable with 1–4 halogen atoms, (b) when $R^2$ is a cycloalkyl group having a carbon number of 3–6 substitutable with an alkyl group having a carbon number of 1–4 or a phenyl group substituted with 1 or more halogen atoms, $R^3$ is a cycloalkyl group having a carbon number of 3–6 substituted with an alkyl group having a carbon number of 1–4 or a phenyl group substituted with 1 or more halogen atoms, (c) when $R^2$ is a phenyl group substituted with a halogen atom, methyl group, nitro group, cyano group or trifluoromethyl group, $R^3$ a β-chloro-1-cycloalkenyl group having a carbon number of 5–15 (the cycloalkenyl group may be substituted with an alkyl group having a carbon number of 1–4);

and $R^2$ and $R^3$ are not same phenyl group substituted with a halogen atom and $R^2$ and $R^3$ are not same cycloalkyl group having a carbon number of 3–6 substituted with an alkyl group having a carbon number of 1–4). Furthermore, the pest controlling agent according to the invention contains such a triazole derivative as an effective ingredient.

In the above general formula, as the alkyl group having a carbon number of 1–4 in $R^1$, the alkyl group having a carbon number of 1–4 substituted to the phenyl group in R2 and the alkyl group having a carbon number of 1–4 substituted to the cycloalkyl group in $R^2$, $R^3$, mention may be made of methyl group, ethyl group, propyl group, isopropyl group, butyl group, isobutyl group, sec-butyl group, tert-butyl group and the like.

As the cycloalkyl group having a carbon number of 3–6 substituted to the alkyl group in $R^2$, $R^3$, mention may be made of cyclopropyl group, cyclopentyl group, cyclohexyl group and the like. As a concrete example of the cycloalkyl group substituted to the alkyl group in $R^2$, $R^3$, there are mentioned 1-methylcyclopropyl group, 2-methylcyclopropyl group, 1-methylcyclopentyl group, 1-methylcyclohexyl group, 2-methylcyclohexyl group, 3-methylcyclohexyl group, 4-methylcyclohexyl group and the like. $R^2$ includes a cycloalkyl group not substituted with an alkyl group, while $R^3$ does not include a cycloalkyl group not substituted with an alkyl group.

As the alkoxy group substituted to the phenyl group in $R^2$, mention may be made of methoxy group, ethoxy group, propoxy group, isobutyloxy group, hexyloxy group and the like.

As the halogen atom substituted to the alkenyl group in $R^3$ and the halogen atom substituted to the phenyl group in $R^2$, $R^3$, mention may be made of fluorine atom, chlorine atom, bromine atom, iodine atom and the like.

The alkenyl group in $R^3$ substitutable with the halogen atom has a carbon number of 3–15 and includes propenyl group, butenyl group, pentenyl group, hexenyl group and the like.

As the β-chloro-1-cycloalkenyl group having a carbon number of 5–15 substitutable with an alkyl group having a carbon number of 1–4 in $R^3$, there are mentioned β-chloro-1-cyclopentenyl group, β-chloro-1-cyclododecenyl group, β-chloro-1-cyclooctenyl group, β-chloro-5-methyl-1-cyclohexenyl group and the like.

The compounds of the general formula [I] according to the invention are exemplified in Tables 1–8. In these tables, as a geometric isomer of alkene, Entogegen body is abbreviated as E and Zusammen body is abbreviated as Z, in which E, Z alone and a mixture of E,Z are included in the invention. And also, compound number is referred in subsequent description.

TABLE 1

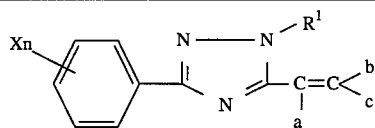

| Compound No. | $R^1$ | Xn | a | b | c | Geometric isomer of alkene | Physical properties melting point (°C.) refractive index ($n_D^{20}$) |
|---|---|---|---|---|---|---|---|
| 1 | $CH_3$ | 2-Cl | H | Cl | $CH_3$ | — | 1.6129 |
| 2 | $CH_3$ | H | $CH_3$ | $CH_3$ | Cl | E | 1.5821 |
| 3 | $CH_3$ | 2-F | $CH_3$ | $CH_3$ | Cl | E | 1.5686 |
| 4 | $CH_3$ | 3-F | $CH_3$ | $CH_3$ | Cl | E | 1.5659 |
| 5 | $CH_3$ | 4-F | $CH_3$ | $CH_3$ | Cl | E | 1.5650 |
| 6 | $CH_3$ | 2-Cl | $CH_3$ | $CH_3$ | Cl | E | 1.5880 |
| 7 | $CH_3$ | 2-Cl | $CH_3$ | Cl | $CH_3$ | Z | 1.5788 |
| 8 | $C_2H_5$ | 2-Cl | $CH_3$ | $CH_3$ | Cl | E | 1.5739 |
| 9 | $CH_3$ | 3-Cl | $CH_3$ | $CH_3$ | Cl | E | 1.5891 |
| 10 | $CH_3$ | 4-Cl | $CH_3$ | $CH_3$ | Cl | E | 1.5919 |
| 11 | $CH_3$ | 2-Br | $CH_3$ | $CH_3$ | Cl | E | 1.6009 |
| 12 | $CH_3$ | 2-I | $CH_3$ | $CH_3$ | Cl | E | 1.6229 |
| 13 | $CH_3$ | 2-$CH_3$ | $CH_3$ | $CH_3$ | Cl | E | 1.5729 |
| 14 | $CH_3$ | 2-$OC_2H_5$ | $CH_3$ | $CH_3$ | Cl | E | 1.5698 |
| 15 | $CH_3$ | 2-$C_3H_7$-i | $CH_3$ | $CH_3$ | Cl | E | 1.5619 |
| 16 | $CH_3$ | 2-$CF_3$ | $CH_3$ | $CH_3$ | Cl | E | 76–82 |
| 17 | $CH_3$ | 4-$CF_3$ | $CH_3$ | $CH_3$ | Cl | E | 54–58 |
| 18 | $CH_3$ | 2-$NO_2$ | $CH_3$ | $CH_3$ | Cl | E | 76–80 |
| 19 | $CH_3$ | 2,6-$F_2$ | $CH_3$ | $CH_3$ | Cl | E | 1.5503 |
| 20 | $CH_3$ | 2,4-$F_2$ | $CH_3$ | $CH_3$ | Cl | E | 52–57 |
| 21 | $CH_3$ | 3,4-$F_2$ | $CH_3$ | $CH_3$ | Cl | E | 68–73 |
| 22 | $CH_3$ | 3,5-$F_2$ | $CH_3$ | $CH_3$ | Cl | E | 1.5516 |
| 23 | $CH_3$ | 2,3-$F_2$ | $CH_3$ | $CH_3$ | Cl | E | 1.5458 |

TABLE 2

| Compound No. | $R^1$ | Xn | a | b | c | Geometric isomer of alkene | Physical properties melting point (°C.) refractive index ($n_D^{20}$) |
|---|---|---|---|---|---|---|---|
| 24 | $CH_3$ | 2,5-$F_2$ | $CH_3$ | $CH_3$ | Cl | E | 59–62 |
| 25 | $CH_3$ | 2-Cl,6-F | $CH_3$ | $CH_3$ | Cl | E | 142–149 |
| 26 | $CH_3$ | 2-F,3-Cl | $CH_3$ | $CH_3$ | Cl | E | 85–96 |
| 27 | $CH_3$ | 2-F,4-Cl | $CH_3$ | $CH_3$ | Cl | E | 75–77 |
| 28 | $CH_3$ | 2-F,6-I | $CH_3$ | $CH_3$ | Cl | E | 1.5920 |
| 29 | $CH_3$ | 2,4-$Cl_2$ | $CH_3$ | $CH_3$ | Cl | — | 72–74 |
| 30 | $CH_3$ | 3,5-$Cl_2$ | $CH_3$ | $CH_3$ | Cl | E | 67–71 |
| 31 | $CH_3$ | 2,3-$Cl_2$ | $CH_3$ | $CH_3$ | Cl | E | 1.5833 |
| 32 | $CH_3$ | 2,5-$Cl_2$ | $CH_3$ | $CH_3$ | Cl | E | 68–73 |

TABLE 2-continued

| Compound No. | $R^1$ | Xn | a | b | c | Geometric isomer of alkene | Physical properties melting point (°C.) refractive index ($n_D^{20}$) |
|---|---|---|---|---|---|---|---|
| 33 | $CH_3$ | 3,4-$Cl_2$ | $CH_3$ | $CH_3$ | Cl | E | 56~59 |
| 34 | $CH_3$ | 2,3,4-$F_3$ | $CH_3$ | $CH_3$ | Cl | E | 60~65 |
| 35 | $CH_3$ | 2,3,6-$F_3$ | $CH_3$ | $CH_3$ | Cl | E | 1.5377 |
| 36 | $CH_3$ | 2,4,5-$F_3$ | $CH_3$ | $CH_3$ | Cl | E | 58.5~63 |
| 37 | $CH_3$ | 2,3,5,6-$F_4$ | $CH_3$ | $CH_3$ | Cl | E | 1.5252 |
| 38 | $CH_3$ | 2,3,4,5-$F_4$ | $CH_3$ | $CH_3$ | Cl | E | 55.5~61 |
| 39 | $CH_3$ | 2,3,4,5,6-$F_5$ | $CH_3$ | $CH_3$ | Cl | E | 79~84 |
| 40 | $CH_3$ | 2-Cl | $CH_3$ | $C_2H_5$ | Cl | E | 1.5797 |
| 41 | $CH_3$ | 2-Cl | $CH_3$ | Cl | $C_2H_5$ | Z | 1.5753 |
| 42 | $CH_3$ | 2-Cl | $C_2H_5$ | $CH_3$ | Cl | — | 1.5770 |
| 43 | $CH_3$ | 2-Br | $C_2H_5$ | $CH_3$ | Cl | E | 1.5901 |
| 44 | $CH_3$ | 2-Br | $CH_3$ | $C_2H_5$ | Cl | E | 1.5899 |
| 45 | $CH_3$ | 2-I | $CH_3$ | $C_2H_5$ | Cl | E | 1.6140 |
| 46 | $CH_3$ | 2-I | $C_2H_5$ | $CH_3$ | Cl | E | 1.6102 |
| 47 | $CH_3$ | 2-$CH_3$ | $CH_3$ | $C_2H_5$ | Cl | E | 1.5701 |
| 48 | $CH_3$ | 2-$CH_3$ | $C_2H_5$ | $CH_3$ | Cl | E | 1.5690 |
| 49 | $CH_3$ | 2,6-$F_2$ | $CH_3$ | $C_2H_5$ | Cl | — | 49~52 |
| 50 | $CH_3$ | 2,6-$F_2$ | $C_2H_5$ | $CH_3$ | Cl | — | 77~78 |

TABLE 3

| Compound No. | $R^1$ | Xn | a | b | c | Geometric isomer of alkene | Physical properties melting point (°C.) refractive index ($n_D^{20}$) |
|---|---|---|---|---|---|---|---|
| 51 | $CH_3$ | 2-Cl,6-F | $CH_3$ | $C_2H_5$ | Cl | E | 98~100 |
| 52 | $CH_3$ | 2-Cl,6-F | $CH_3$ | Cl | $C_4H_5$ | Z | 1.5548 |
| 53 | $CH_3$ | 2-Cl,6-F | $C_2H_5$ | $CH_3$ | Cl | E | 117~119 |
| 54 | $CH_3$ | 2-Cl | H | Cl | $C_4H_9$-i | Z | 1.5802 |
| 55 | $CH_3$ | 2-Cl | $CH_3$ | $C_3H_7$ | Cl | — | 1.5732 |
| 56 | $CH_3$ | 2-Cl | $C_3H_7$ | $CH_3$ | Cl | — | 1.5709 |
| 57 | $CH_3$ | 2-Cl | $C_4H_9$ | $CH_3$ | Cl | — | 1.5614 |
| 58 | $CH_3$ | 2-$CH_3$ | $C_4H_9$ | $CH_3$ | Cl | — | |
| 59 | $CH_3$ | 2-$CF_3$ | $C_4H_9$ | $CH_3$ | Cl | — | |
| 60 | $CH_3$ | 2-CN | $C_4H_9$ | $CH_3$ | Cl | — | |
| 61 | $CH_3$ | 2-$OCH_3$ | $C_4H_9$ | $CH_3$ | Cl | — | |
| 62 | $CH_3$ | 2-$NO_2$ | $C_4H_9$ | $CH_3$ | Cl | — | |
| 63 | $CH_3$ | 2,6-$F_2$ | $C_4H_9$ | $CH_3$ | Cl | — | |
| 64 | $CH_3$ | 2-Cl,6-F | $C_4H_9$ | $CH_3$ | Cl | — | |
| 65 | $CH_3$ | 2,6-$Cl_2$ | $C_4H_9$ | $CH_3$ | Cl | — | |
| 66 | $CH_3$ | 2-Cl | $C_4H_9$-i | $CH_3$ | Cl | — | 1.5604 |
| 67 | $CH_3$ | 2-Cl | $C_5H_{11}$ | $CH_3$ | Cl | — | 1.5594 |
| 68 | $CH_3$ | 2-Cl | $C_6H_{13}$ | $CH_3$ | Cl | — | 1.5558 |
| 69 | $CH_3$ | 2-Cl | $C_6H_{13}$ | Cl | $CH_3$ | — | 1.5508 |
| 70 | $CH_3$ | 2-Cl | H | H | $C_6H_{13}$ | — | 1.5620 |
| 71 | $CH_3$ | 2-I | $C_7H_{15}$ | $CH_3$ | Cl | — | 1.5737 |
| 72 | $CH_3$ | 2,6-$F_2$ | $C_7H_{15}$ | $CH_3$ | Cl | — | 1.5194 |
| 73 | $CH_3$ | 2-Cl | $C_8H_{17}$ | $CH_3$ | Cl | — | 1.5446 |
| 74 | $CH_3$ | 2-Cl | $C_9H_{19}$ | $CH_3$ | Cl | — | 1.5401 |
| 75 | $CH_3$ | 2-Cl | $C_{10}H_{21}$ | $CH_3$ | Cl | — | 1.5395 |
| 76 | $CH_3$ | 2-Cl | $C_{11}H_{23}$ | $CH_3$ | Cl | — | 1.5329 |
| 77 | $CH_3$ | 2-Cl | $C_{12}H_{25}$ | $CH_3$ | Cl | — | 1.5358 |

TABLE 4

| Compound No. | $R^1$ | Xn | a | b | c | Geometric isomer of alkene | Physical properties melting point (°C.) refractive index ($n_D^{20}$) |
|---|---|---|---|---|---|---|---|
| 78 | $CH_3$ | 2,6-$F_2$ | $C_{12}H_{25}$ | $CH_3$ | Cl | — | 1.5095 |
| 79 | $CH_3$ | 2-Cl | $C_3H_7$ | $C_4H_9$ | Cl | — | 1.5615 |
| 80 | $CH_3$ | 2-Cl | $CH_3$ | $C_5H_{11}$ | Cl | — | 1.5592 |
| 81 | $CH_3$ | 2-Cl | $CH_3$ | Cl | $C_5H_{11}$ | — | 1.5591 |

TABLE 5

$$\underset{R^2}{\overset{N-N-R^1}{\underset{N}{\parallel}}}R^3$$

| Compound No. | R¹ | R² | R³ | Physical properties melting point (°C.) refractive index ($n_D^{20}$) |
|---|---|---|---|---|
| 82 | CH₃ | 2-Cl-phenyl | 1-methylcyclopropyl | 1.5694 |
| 83 | CH₃ | 2-Cl-phenyl | 1-methylcyclopentyl | 1.5718 |
| 84 | CH₃ | 2-Cl-phenyl | 1-methylcyclohexyl | 1.5684 |
| 85 | CH₃ | 2-Cl-phenyl | 4-methylcyclohexyl | 1.5581 |
| 86 | CH₃ | 2-Cl-phenyl | 2-methylcyclohexyl | 1.5589 |

TABLE 6

| Compound No. | R¹ | R² | R³ | Physical properties melting point (°C.) refractive index ($n_D^{20}$) |
|---|---|---|---|---|
| 87 | CH₃ | 2-Cl-phenyl | 4-methylcyclohexyl | 1.5595 |
| 88 | CH₃ | 2-Cl-phenyl | 1-methylcyclopropyl | 1.5754 |
| 89 | CH₃ | 2-Cl-6-F-phenyl | 1-methylcyclohexyl | 91~95 |
| 90 | CH₃ | 2-Cl-6-F-phenyl | 2-methylcyclohexyl | 1.5469 |
| 91 | CH₃ | 1-methylcyclopropyl | 2-Cl-phenyl | 1.5621 |
| 92 | CH₃ | cyclohexyl | 2-Cl-phenyl | 1.5579 |
| 93 | CH₃ | 2-methylcyclohexyl | 2-Cl-phenyl | 1.6095 |
| 94 | CH₃ | 1-methylcyclohexyl | 2-Cl-phenyl | 71~73 |

TABLE 7

$$\underset{}{\overset{Xn}{\underset{}{\bigcirc}}}\underset{N}{\overset{N-N-R^1}{\underset{\parallel}{\parallel}}}R^3$$

| Compound No. | R¹ | Xn | Carbon number in ring of R³ | R³ | Physical properties melting point (°C.) refractive index ($n_D^{20}$) |
|---|---|---|---|---|---|
| 95 | CH₃ | 2-Cl | 5 | 2-Cl-cyclopentenyl | 57~58 |
| 96 | CH₃ | 2-Cl,6-F | 5 | 2-Cl-cyclopentenyl | — |
| 97 | CH₃ | 2-F | 6 | 2-Cl-cyclohexenyl | — |
| 98 | CH₃ | 2-Cl | 6 | 2-Cl-cyclohexenyl | 69~72 |

TABLE 7-continued

| Compound No. | R¹ | Xn | Carbon number in ring of R³ | R³ | Physical properties melting point (°C.) refractive index ($n_D^{20}$) |
|---|---|---|---|---|---|
| 99 | CH₃ | 2-Br | 6 | cyclohexenyl-Cl | 75~77 |
| 100 | CH₃ | 2-I | 6 | cyclohexenyl-Cl | 1.6311 |
| 101 | CH₃ | 2-Cl,6-F | 6 | cyclohexenyl-Cl | 105~107 |
| 102 | CH₃ | 2,6-F₂ | 6 | cyclohexenyl-Cl | — |
| 103 | CH₃ | 2-CH₃ | 6 | cyclohexenyl-Cl | — |
| 104 | CH₃ | 2-NO₂ | 6 | cyclohexenyl-Cl | — |
| 105 | CH₃ | 2-CN | 6 | cyclohexenyl-Cl | — |

TABLE 8

| Compound No. | R¹ | Xn | Carbon number in ring of R³ | R³ | Physical properties melting point (°C.) refractive index ($n_D^{20}$) |
|---|---|---|---|---|---|
| 106 | CH₃ | 2-CF₃ | 6 | cyclohexenyl-Cl | — |
| 107 | CH₃ | 2-Cl | 7 | cycloheptenyl-Cl | 1.5942 |
| 108 | CH₃ | 2-Cl,6-F | 7 | cycloheptenyl-Cl | — |

TABLE 8-continued

| Compound No. | R¹ | Xn | Carbon number in ring of R³ | R³ | Physical properties melting point (°C.) refractive index ($n_D^{20}$) |
|---|---|---|---|---|---|
| 109 | $CH_3$ | 2-Cl | 8 | (cyclooctenyl with Cl) | 1.5920 |
| 110 | $CH_3$ | 2-Cl,6-F | 8 | (cyclooctenyl with Cl) | — |
| 111 | $CH_3$ | 2-Cl | 12 | (cyclododecenyl with Cl) | — |
| 112 | $CH_3$ | 2-Cl,6-F | 12 | (cyclododecenyl with Cl) | — |
| 113 | $CH_3$ | 2-Cl | 6 | (6-methyl-2-chlorocyclohexenyl) | 115–116.5 |
| 114 | $CH_3$ | 2-Br | 6 | (6-methyl-2-chlorocyclohexenyl) | — |
| 115 | $CH_3$ | 2-Cl,6-F | 6 | (6-methyl-2-chlorocyclohexenyl) | — |
| 116 | $CH_3$ | 2,6-$F_2$ | 6 | (6-methyl-2-chlorocyclohexenyl) | — |

The compounds according to the invention can be produced according to the following methods, but the invention is not limited to these methods.

Production Method <A>

(Reaction formula 1)

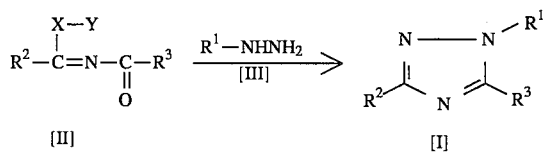

[II]                                   [I]

(wherein X is a sulfur atom or an oxygen atom, Y is an alkyl group having a carbon number of 1–4, and R¹, R² and R³ are the same as mentioned above.)

That is, the compound according to the invention represented by the general formula [I] can be obtained by reacting N-acylimino acid ester or thioimino acid ester derivative represented by a general formula [II] with a hydrazine derivative represented by a general formula [III] in an inert solvent.

As the solvent, any solvents not obstructing the reaction can be used, which include, for example, ethers such as diethyl ether, tetrahydrofuran, dioxane, diglyme and so on; aromatic hydrocarbons such as benzene, toluene, chlorobenzene and so on; aliphatic hydrocarbons such as pentane, hexane, petroleum ether and so on; halogenated hydrocarbons such as dichloromethane, dichloroethane, chloroform, carbon tetrachloride and so on; nitriles such as acetonitrile and so on; non-protonic polar solvents such as dimethylformamide, dimethylacetamide, dimethylsulfoxide and so on; and water. Further, there may be used a mixed solvent comprised of a combination of solvents selected from the above.

Furthermore, the amount of the reactant used is usually 1.0–5.0 moles of the compound shown by the general formula [III] per 1 mole of the compound shown by the general formula [II]. The reaction temperature is optional within a range of from 0° C. to a boiling point of the solvent, but the reaction is preferably carried out within a range of 0° C.–50° C. The reaction time is different in accordance with the compound, but the object can usually be attained for 1 hour–72 hours. The detail of this reaction is, for example, described in Synthesis, page 483 (1983).

And also, the compound shown by the general formula [II] as a starting material can be produced according to the following method.

Production Method <B>

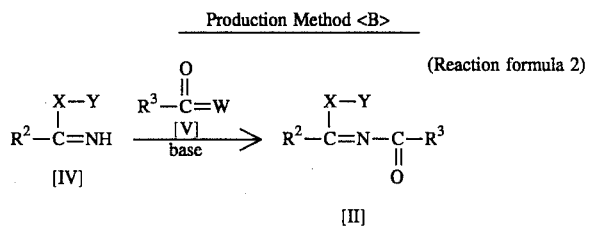

(Reaction formula 2)

[wherein W is a halogen atom, and X, Y, $R^2$ and $R^3$ are the same as mentioned above.]

That is, the compound of the general formula [II] can be produced by reacting s compound of a general formula [IV] and a compound of a general formula [V] in the presence of a base in an inert solvent. The compound of the general formula [IV] may be an addition salt such as a salt with boron tetrafluoride, hydrogen chloride, hydrogen bromide, hydrogen iodide or the like.

As the base, use may be made of inorganic bases such as sodium carbonate, potassium carbonate, sodium hydrogen carbonate, sodium hydroxide, potassium hydroxide and the like; and organic bases such as diethylamine, triethylamine, pyridine, 4-N,N-dimethylamino pyridine and the like. As the solvent, use may be made of ketones such as acetone, methyl ethyl ketone and so on; ethers such as diethyl ether, tetrahydrofuran, dioxane, diglyme and so on; aromatic hydrocarbons such as benzene, toluene, chlorobenzene and so on; aliphatic hydrocarbons such as pentane, hexane, petroleum ether and the like; halogenated hydrocarbons such as dichloromethane, dichloroethane, chloroform, carbon tetrachloride and so on; nitriles such as acetonitrile and so on; nonprotonic polar solvents such as dimethylformamide, dimethylacetamide, dimethylsulfoxide and so on; and water. Further, there may be used a mixed solvent comprised of a combination of solvents selected from the above.

The amount of the reactant used is usually 0.8–1.3 moles of the compound shown by the general formula [V] per 1 mole of the compound shown by the general formula [IV]. The amount of the base used is 1.0–2.0 times equivalent per 1 mole of the compound shown by the general formula [IV]. The reaction time is different in accordance with the compound but is usually within a range of 1 hour-24 hours. The reaction temperature is within a range of from 0° C. to a boiling point of the solvent.

BEST MODE FOR CARRYING OUT THE INVENTION

The production method of the compounds according to the invention will be concretely described with reference to the following examples.

EXAMPLE 1

Production of (E)-5-(2-chloro-1-methyl-1-propenyl)-3-(2-chlorophenyl)-1-methyl-1H-1,2,4-triazole (Compound 6)

Ethyl 2-chlorobenzimidate (2.80 g) and triethylamine (1.70 g) are dissolved in toluene (50 ml), to which is added dropwise (E)-3-chloro-2-methyl-2-butenoyl chloride at 5° C.–10° C. with stirring, and the stirring is continued at room temperature for 4 hours after the completion of the addition. After the completion of the reaction, the reaction mixture is added with toluene (150 ml), washed with a saline solution, dried on anhydrous magnesium sulfate and concentrated under a reduced pressure. The concentrate is purified through a silica gel column chromatography (Wakogel C-200: made by Wako Junyaku Kabushiki Kaisha) using a mixed solution of hexane-ethyl acetate (10:1) as a developing medium to obtain an oily ethyl (E)-N-(3-chloro-1-methyl-2-butenoyl)-2-chlorobenzimidate (2.37 g).

The thus obtained N-acylimidate is dissolved in toluene (50 ml), added with methylhydrazine (1.0 g) and stirred at room temperature for 4 hours. After the completion of the reaction, the reaction mixture is concentrated under a reduced pressure and then the resulting concentrate is purified through a silica gel column chromatography (Wakogel C-200: made by Wako Junyaku Kabushiki Kaisha) using a mixed solution of hexane-ethyl acetate (10:1) as a developing medium to obtain 1.67 g of an objective compound as a light yellow viscous liquid (refractive index: $n_D^{20}$=1.5880).

The NMR data of the resulting compound are as follows.

| NMR data (400 MHz, $CDCl_3$ solvent, δ value, ppm) | |
|---|---|
| 2.09 | (3H, q, J=1.60 HZ) |
| 2.18 | (3H, q, J=1.60 HZ) |
| 3.84 | (3H, s) |
| 7.30–7.50 | (3H, m) |
| 7.85–7.91 | (1H, m) |

EXAMPLE 2

Production of (E)-5-(2-chloro-1-methyl-1-propenyl)-3-(4-chloro-2-fluorophenyl)-1-methyl-1H-1,2,4-triazole (Compound 27)

Ethyl 4-chloro-2-fluorobenzimidate (3.0 g), triethylamine (1.5 g) and (E)-3-chloro-2-methyl-2-butenoyl chloride are dissolved in toluene (100 ml), stirred at room temperature for 1 hour and further refluxed under heating for 4 hours. After the completion of the reaction, the reaction mixture is added with water and then the resulting toluene layer is dried on anhydrous magnesium sulfate.

The reaction solution is added with methylhydrazine (1.0 g) and stirred at room temperature for 48 hours. After the completion of the reaction, it is washed with a diluted hydrochloric acid and further with water, dried on anhydrous magnesium sulfate and then concentrated. It is purified through a silica gel column chromatography using a mixed solution of hexaneethyl acetate (10:1) as a developing medium to obtain 1.75 g of an objective compound as a colorless needle crystal (melting point 75°–77° C).

The NMR data of the resulting compound are as follows.

| NMR data (60 MHz, $CDCl_3$ solvent, δ value, ppm) | |
|---|---|
| 1.80–2.30 | (6H, m) |
| 3.81 | (3H, s) |
| 7.00–8.15 | (3H, m) |

EXAMPLE 3

Production of 5-(1-butyl-2-chloro-1-propenyl)-3-(2-chlorophenyl)-1-methyl-1H-1,2,4-triazole (Compound 57)

Ethyl 2-chlorobenzimidate (2.02 g), potassium carbonate (1.52 g), (E,Z)-3-chloro-2-butyl-2-butenoyl chloride (2.55 g) are dissolved in acetone (50 ml) and stirred under reflux by heating for 4 hours. After the completion of the reaction, the reaction mixture is added with water (150 ml), extracted with ether (200 ml) two times, washed with a saline solution, dried on anhydrous magnesium sulfate and concentrated under a reduced pressure.

The concentrate is dissolved in dioxane (50 ml), added with methylhydrazine (1.30 g) and stirred at room temperature for 48 hours. After the completion of the reaction, the reaction mixture is added with toluene (250 ml), washed with a diluted hydrochloric acid and further with a saturated saline solution, dried on anhydrous magnesium sulfate and concentrated under a reduced pressure. The concentrate is purified through a silica gel column chromatography using a mixed solution of hexane-ethyl acetate (10:1) as a developing medium to obtain 1.31 g of an objective compound as a light yellow viscous liquid (refractive index: $n_D^{20}$= 1.5614).

The NMR data of the resulting compound are as follows.

| NMR data (60 MHz, CDCl$_3$ solvent, δ value, ppm) | |
|---|---|
| 0.88 | (3H, t) |
| 1.20–1.52 | (4H, m) |
| 2.04 | (3H, s) |
| 2.62 | (2H, t) |
| 3.84 | (3H, s) |
| 7.22–8.10 | (4H, m) |

EXAMPLE 4

Production of 5-(2-chloro-1-octyl-1-propenyl)-3-(2-chlorophenyl)-1-methyl-1H-1,2,4-triazole (Compound 73)

Ethyl 2-chlorobenzimidate (1.93 g) and 3-chloro-2-octyl-2-butenoyl chloride (2.52 g) are dissolved in toluene (30 ml), to which is added dropwise triethylamine (0.85 g) at 5° C.–10° C. with stirring and thereafter stirred at room temperature for 4 hours. After the completion of the reaction, the reaction mixture is added with toluene (150 ml), washed with a diluted hydrochloric acid and further with a saturated saline solution, and dried on anhydrous magnesium sulfate.

The resulting reaction solution is added with methylhydrazine (1.0 g) and stirred at room temperature for 4 hours. After the completion of the reaction, the reaction mixture is washed with a diluted hydrochloric acid and further with a saturated saline solution, dried on anhydrous magnesium sulfate and concentrated under a reduced pressure. The concentrate is purified through a silica gel column chromatography using a mixed solution of hexane-ethyl acetate (15:1) as a developing medium to obtain 1.12 g of an objective compound as a light yellow viscous liquid (refractive index: $n_D^{20}$=1.5446).

The NMR data of the resulting compound are as follows.

| NMR data (60 MHz, CDCl$_3$ solvent, δ value, ppm) | |
|---|---|
| 0.85–1.70 | (15H, m) |
| 2.03 | (3H, s) |
| 2.64 | (2H, t) |
| 3.86 | (3H, s) |
| 7.13–8.03 | (4H, m) |

EXAMPLE 5

Production of 5-(2-chloro-1-dodecyl-1-propenyl)-3-(2,6-difluorophenyl)-1-methyl-1H-1,2,4-triazole (Compound 78)

Ethyl 2,6-difluorobenzimidate (1.50 g) and triethylamine (0.85 g) are dissolved in toluene (30 ml), to which is added dropwise 3-chloro-2-dodecyl-2-butenoyl chloride (2.50 g) and thereafter stirred at room temperature for 12 hours. After the completion of the reaction, the reaction mixture is added with toluene (150 ml), washed with a diluted hydrochloric acid and further with a saturated saline solution, and dried on anhydrous magnesium sulfate.

The resulting reaction solution is added with methylhydrazine (0.8 g) and stirred at room temperature for 4 hours. After the completion of the reaction, the reaction mixture is washed with a diluted hydrochloric acid and further with a saturated saline solution, dried on anhydrous magnesium sulfate and concentrated under a reduced pressure. The concentrate is purified through a silica gel column chromatography using a mixed solution of hexane-ethyl acetate (15:1) as a developing medium to obtain 0.83 g of an objective compound as a light yellow viscous liquid (refractive index: $n_D^{20}$=1.5095).

The NMR data of the resulting compound are as follows.

| NMR data (60 MHz, CDCl$_3$ solvent, δ value, ppm) | |
|---|---|
| 0.85–1.70 | (23H, m) |
| 2.05 | (3H, s) |
| 2.63 | (2H, t) |
| 3.87 | (3H, s) |
| 7.10–7.90 | (3H, m) |

Example 6

Production of 3-(2-chloro-6-fluorophneyl)-1-methyl-5-(1-methylcyclohexyl)-1H-1,2,4-triazole (Compound 89)

Ethyl 2-chloro-6-fluoro-benzimidate (1.61 g) and triethylamine (1.0 g) are dissolved in toluene (100 ml), to which is added dropwise 1-methylcyclohexylcarbonyl chloride (1.5 g) at 5°–10° C. with stirring and thereafter stirred at room temperature for 1 hour. Further, it is reacted at 80°–100° C. for 16 hours. After the completion of the reaction, the reaction solution is washed with a saline solution and further with water and then the resulting toluene layer is dried on sodium sulfate and concentrated to obtain crude product of ethyl N-(1-methylcyclohexylcarbonyl)-2-chloro-6-fluorobenzimidate.

The thus obtained crude product is dissolved in 200 ml of toluene, added with monomethylhydrazine (2.0 g) and reacted at room temperature for 10 hours. After the completion of the reaction, it is washed with a diluted hydrochloric acid and further with water, and the resulting toluene layer is dried on anhydrous magnesium sulfate and concentrated under a reduced pressure. The concentrate is purified through a silica gel column chromatography using a mixed solution of hexane-ethyl acetate as a developing medium to obtain 0.56 g of an objective compound as a colorless granular crystal (melting point=91°–95° C.).

The NMR data of the resulting compound are as follows.

| NMR data (60 MHz, CDCl$_3$ solvent, δ value, ppm) | |
|---|---|
| 0.70–0.94 | (3H, m) |
| 1.00–2.60 | (9H, m) |
| 3.00 | (1H, q) |
| 3.85 | (3H, s) |
| 6.73–7.30 | (3H, m) |

EXAMPLE 7

Production of 5-(β-chloro-1-cyclohexenyl)-3-(2-chlorophenyl)-1-methyl-1H-1,2,4-triazole (Compound 98)

Methyl 2-chlorobenzthiol imidate-hydroiodide (2.2 g) and triethylamine (1.5 g) are dissolved in tetrahydrofuran (50 ml), to which is added dropwise β-chloro-1-cyclohexenecarbonyl chloride (1.3 g) at 5°–10° C. with stirring. They are reacted by stirring at room temperature for 1 hour and then stirring at room temperature over a night. After the completion of the reaction, it is dissolved in toluene (200 ml) and washed with water, and thereafter the resulting toluene layer is dried on anhydrous magnesium sulfate. After the concentration, it is subjected to a silica gel column chromatography to obtain 2.1 g of an imide intermediate.

The thus obtained imide is dissolved in toluene (50 ml), added with monomethylhydrazine (0.3 g) and reacted at room temperature for 24 hours. After the completion of the reaction, it is added with toluene (200 ml), washed with water, and the resulting toluene layer is dried on anhydrous magnesium sulfate, concentrated and subjected to a silica gel column chromatography using a mixed solution of hexane-ethyl acetate (25:1) as a developing medium to obtain 1.23 g of an objective compound as a colorless granular crystal (melting point=69°–72° C.).

The NMR data of the resulting compound are as follows.

| NMR data (60 MHz, CDCl$_3$ solvent, δ value, ppm) | |
|---|---|
| 1.70–2.10 | (4H, m) |
| 2.20–2.60 | (4H, m) |
| 3.8 | (3H, s) |
| 7.10–8.10 | (4H, m) |

EXAMPLES 8–19

Compounds (82)-(88), (90)-(94) shown in Tables 5–6 are produced in the same manner as in Example 6.

EXAMPLES 20–28

Compounds (95), (97), (99)-(101), (106), (107), (109), (113) shown in Tables 7–8 are produced in the same manner as in Example 7.

The pest controlling agent according to the invention contains the triazole derivative shown by the general formula [I] as an active ingredient. When the compounds according to the invention are used in the pest controlling agent, these compounds themselves may be used alone, or may be compounded with a carrier, a surfactant, a dispersing agent, an adjuvant or the like, which is usually used in the formulation, to form dust, wettable powder, emulsion, fine powder, granulate or the like.

As the carrier used in the formulation, mention may be made of a solid carrier such as zeeklite, talc, bentonite, clay, kaolin, diatomaceous earth, white carbon, vermiculite, calcium hydroxide, quartz sand, ammonium sulfate, urea or the like; and a liquid carrier such as isopropyl alcohol, xylene, cyclohexanone, methylnaphthalene or the like. As the surfactant and dispersing agent, mention may be made of a metal salt of alkylbenzene sulfonic acid, a metal salt of dinaphthylmethane disulfonic acid, a sulfuric acid ester of alcohol, alkylarylsulfonate, lignin sulfonate, polyoxyethylene glycol ether, polyoxyethylene alkylaryl ether, polyoxyethylene sorbitan monoalkylate and the like. As the adjuvant, mention may be made of carboxymethylcellulose, polyethylene glycol, gum arabic and the like.

The amount of the active ingredient used may be properly selected in accordance with the use purpose, but it is properly selected within a range of 0.05–20% (by weight), preferably 0.1–10% (by weight) in case of the dust and granulate. In case of the emulsion and wettable powder, it is properly selected within a range of 0.5–80% (by weight), preferably 1–60% (by weight).

In use, the active ingredient is sprayed by diluting to a proper concentration or directly applied. The pest controlling agent according to the invention may be used by spraying onto stem and leaves, by applying to soil, by applying to a nursery box, by spraying onto water surface or the like. The amount of the pest controlling agent applied is dependent upon the kind of the compound used, injurious insect to be controlled, tendency and degree of insect injury, environmental condition, kind of formulation used and the like. When the pest controlling agent is directly used as dust or granulate, the amount of the active ingredient is properly selected within a range of 0.05 g–5 kg, preferably 0.1 g–1 kg per 10 are. Furthermore, when it is used in form of a liquid as emulsion or wettable powder, the amount of the active ingredient is properly selected within a range of 0.1–5000 ppm, preferably 1–1,000 ppm.

Moreover, the pest controlling agent according to the invention may be used by mixing with other insecticide, fungicide, herbicide, fertilizer, plant growth regulator and the like.

The formulation will concretely be described with respect to typical examples. In this case, the kind of the compounds and additives and the compounding ratio are not limited to these examples and may be varied within wide ranges. Moreover, % is by weight otherwise specified.

Formulation Example 1: Emulsion

An emulsion is prepared by uniformly dissolving 30% of the compound (2), 20% of cyclohexanone, 11% of polyoxyethylene alkylaryl ether, 4% of calcium alkylbenzene sulfonate and 35% of methylnaphthaline. It is applied by diluting with water.

Formulation Example 2: Wettable powder

A wettable powder is prepared by uniformly mixing and pulverizing 40% of the compound (67), 15% of diatomaceous earth, 15% of clay, 25% of white carbon, 2% of sodium dinaphthylmethane disulfonate and 3% of sodium lignin sulfonate. It is applied by diluting with water.

Formulation Example 3: Dust

A dust is prepared by uniformly mixing and pulverizing 2% of the compound (51), 5% of diatomaceous earth and 93% of clay. It is directly applied.

Formulation Example 4: Granulate

5% of the compound (57), 2% of sodium salt of lauryl alcohol sulfuric acid ester, 5% of sodium lignin sulfonate, 2% of carboxymethylcellulose and 86% of clay are mixed and pulverized uniformly. Then, 100 parts by weight of the mixture is added with 20 parts by weight of water and kneaded and shaped into granulates of 14–32 mesh through an extrusion type granulating machine and dried to prepare granulates. They are directly applied.

INDUSTRIAL APPLICABILITY

The triazole derivatives according to the invention have an excellent insecticidal action against planthoppers such as brown planthopper, white-backed planthopper, small brown planthopper and the like; leafhoppers such as green rice leafhopper, tea green leafhopper and the like; aphids such as cotton aphid, green peach aphid, cabbage aphid and the like; whiteflies such as greenhouse whitefly and the like; hemipteran injurious insects such as scales, e.g. mulberry scale or the like and bugs, e.g. corbett rice bug or the like; lepidopteran injurious insects such as diamond-back moth, lima-bean cutworm, tobacco cutworm and the like; dipteran injurious insects such as house fly, mosquito and the like; elytron injurious insects such as rice plant weevil, soy bean weevil, cucurbit leaf beetle and the like; orthopteran injurious insects such as American cockroach, German cockroach and the like; and mites such as two-spotted spider mite, kanzawa spider mite, citrus red mite and the like, and also have an excellent ovicidal action against eggs of the injurious insects. Furthermore, the compounds according to the invention exhibit a preventively high controlling effect against serious diseases such as sheath blight, blast and the like without badly affecting crops.

The effect of the compound according to the invention will be described with respect to the following test examples. Moreover, the following compounds as described in the specification of U.S. Pat. No. 4414221 are used as a comparative chemical in the test.

Comparative chemical A:3-(o-chlorophenyl)-5-cyclohexyl-1-methyl-1M-1,2,4-triazole Comparative chemical B:3-(o-chlorophenyl)-5-ethyl-1-methyl-1H-1,2,4-triazole Comparative chemical C:3-(o-chlorophenyl)-5-(o-chlorophenyl)-1-methyl-1M-1,2,4-triazole Comparative chemical D:3-(o-chlorophenyl)-5-(m-methylphenyl)-1-methyl-1M-1,2,4-triazole

Test Example 1: Insecticidal test for brown planthopper

The wettable powder prepared according to Formulation Example 2 is diluted with water so that the concentration of the active ingredient is 500 ppm. In the resulting diluted wettable powder are immersed rice stems and leaves, which are then dried in air and placed in a test tube. In the test tube are released 10 larvae of brown planthopper and then the opening of the test tube is plugged with absorbent wadding. Thereafter, the test tube is placed in a thermostatic chamber of 25° C. for 6 days and then the number of larvae died is counted to calculate the percentage of mortality. The test is carried out by double series. The results are shown in Table 9.

TABLE 9

| Compound No. | Mortality (%) |
| --- | --- |
| 2 | 95 |
| 3 | 100 |
| 4 | 95 |
| 5 | 100 |
| 6 | 100 |
| 8 | 100 |
| 10 | 90 |
| 11 | 100 |

TABLE 9-continued

| Compound No. | Mortality (%) |
| --- | --- |
| 12 | 100 |
| 13 | 100 |
| 19 | 100 |
| 20 | 100 |
| 25 | 100 |
| 28 | 100 |
| 34 | 95 |
| 35 | 90 |
| 40 | 100 |
| 42 | 100 |
| 43 | 100 |
| 44 | 100 |
| 45 | 100 |
| 46 | 100 |
| 47 | 100 |
| 49 | 100 |
| 50 | 100 |
| 51 | 100 |
| 52 | 95 |
| 53 | 100 |
| 55 | 100 |
| 56 | 100 |
| 82 | 100 |
| 84 | 95 |
| 90 | 100 |
| 94 | 100 |
| Comparative chemical A | 15 |
| Comparative chemical B | 10 |
| Comparative chemical C | 25 |
| Comparative chemical D | 60 |

Test Example 2: Insecticidal test for green rice leafhopper

The wettable powder prepared according to Formulation Example 2 is diluted with water so that the concentration of the active ingredient is 500 ppm. In the resulting diluted wettable powder are immersed rice stems and leaves, which are then dried in air and placed in a test tube. In the test tube are released 5 larvae of green rice leafhopper and then the opening of the test tube is plugged with absorbent wadding. Thereafter, the test tube is placed in a thermostatic chamber of 25° C. for 5 days and then the number of larvae died is counted to calculate the percentage of mortality. The test is carried out by double series. The results are shown in Table 10.

TABLE 10

| Compound No. | Mortality (%) |
| --- | --- |
| 2 | 100 |
| 3 | 100 |
| 4 | 100 |
| 5 | 100 |
| 6 | 100 |
| 8 | 100 |
| 9 | 100 |
| 10 | 100 |
| 11 | 100 |
| 12 | 100 |
| 13 | 100 |
| 15 | 100 |
| 19 | 100 |
| 20 | 100 |
| 21 | 100 |

TABLE 10-continued

| Compound No. | Mortality (%) |
|---|---|
| 22 | 100 |
| 24 | 100 |
| 25 | 100 |
| 28 | 100 |
| 32 | 100 |
| 34 | 100 |
| 35 | 100 |
| 36 | 100 |
| 37 | 100 |
| 38 | 100 |
| 40 | 100 |
| 42 | 100 |
| 43 | 100 |
| 44 | 100 |
| 45 | 100 |
| 46 | 100 |
| 47 | 100 |
| 48 | 100 |
| 49 | 100 |
| 50 | 100 |
| 51 | 100 |
| 52 | 100 |
| 53 | 100 |
| 55 | 100 |
| 56 | 100 |
| 57 | 100 |
| 66 | 100 |
| 82 | 100 |
| 83 | 100 |
| 84 | 90 |
| 85 | 100 |
| 86 | 90 |
| 87 | 100 |
| 89 | 100 |
| 90 | 100 |
| 91 | 100 |
| 92 | 100 |
| Comparative chemical A | 10 |
| Comparative chemical B | 0 |
| Comparative chemical C | 40 |
| Comparative chemical D | 10 |

Test Example 3: Insecticidal test for cotton aphid

The wettable powder prepared according to Formulation Example 2 is diluted with water so that the concentration of the active ingredient is 100 ppm. In the resulting diluted wettable powder are immersed cucumber seedlings previously inoculated with larvae of cotton aphid and then dried in air. After the treatment, the cucumber seedlings are placed in a thermostatic chamber of 25° C. for 3 days and then the number of larvae died is counted to calculate the percentage of mortality. The test is carried out by double series. The results are shown in Table 11.

TABLE 11

| Compound No. | Mortality (%) |
|---|---|
| 3 | 100 |
| 6 | 100 |
| 8 | 100 |
| 11 | 100 |
| 12 | 100 |
| 13 | 100 |
| 18 | 100 |
| 19 | 100 |

TABLE 11-continued

| Compound No. | Mortality (%) |
|---|---|
| 20 | 100 |
| 25 | 100 |
| 28 | 100 |
| 29 | 100 |
| 31 | 100 |
| 35 | 100 |
| 40 | 100 |
| 42 | 100 |
| 43 | 100 |
| 44 | 100 |
| 45 | 100 |
| 46 | 100 |
| 47 | 100 |
| 48 | 100 |
| 49 | 100 |
| 50 | 100 |
| 51 | 100 |
| 52 | 100 |
| 53 | 100 |
| 55 | 100 |
| 56 | 100 |
| 57 | 100 |
| 66 | 100 |
| 67 | 100 |
| 69 | 100 |
| 72 | 100 |
| 73 | 100 |
| 75 | 95 |
| 77 | 100 |
| 80 | 100 |
| 81 | 100 |
| 82 | 100 |
| 83 | 100 |
| 84 | 90 |
| 85 | 100 |
| 86 | 90 |
| 87 | 100 |
| 89 | 100 |
| 90 | 100 |
| 91 | 100 |
| 92 | 100 |
| 95 | 100 |
| 98 | 100 |
| 99 | 100 |
| 100 | 100 |
| 101 | 100 |
| 107 | 95 |
| 109 | 100 |
| Comparative chemical A | 10 |
| Comparative chemical B | 0 |

Test Example 4: Ovicidal test for two-spotted spider mite (concentration: 100 ppm)

Female adults of two-spotted spider mite are placed on three leaf discs of kidney bean (diameter:15 mm) and oviposited over 24 hours, and thereafter these adults are removed therefrom. The wettable powder prepared according to Formulation Example 2 is diluted with water so that the concentration of the active ingredient is 100 ppm and sufficiently applied to these leaf discs. After the treatment, the leaf discs are placed in a thermostatic chamber of 25° C. for 7 days and then the number of unhatched eggs is counted to calculate the percentage of ovicidal activity. The test is carried out by double series. The results are shown in Table 12.

TABLE 12

| Compound No. | Ovicidal activity (%) |
|---|---|
| 3 | 100 |
| 6 | 100 |
| 7 | 100 |
| 8 | 100 |
| 11 | 100 |
| 12 | 100 |
| 19 | 100 |
| 20 | 100 |
| 25 | 100 |
| 28 | 100 |
| 31 | 100 |
| 35 | 100 |
| 40 | 100 |
| 42 | 100 |
| 43 | 100 |
| 44 | 100 |
| 45 | 100 |
| 46 | 100 |
| 47 | 100 |
| 48 | 100 |
| 49 | 100 |
| 50 | 100 |
| 51 | 100 |
| 52 | 100 |
| 53 | 100 |
| 55 | 100 |
| 56 | 100 |
| 57 | 100 |
| 67 | 100 |
| 68 | 100 |
| 69 | 100 |
| 72 | 100 |
| 74 | 94 |
| 82 | 100 |
| 83 | 100 |
| 84 | 95 |
| 85 | 100 |
| 86 | 100 |
| 87 | 100 |
| 88 | 100 |
| 91 | 100 |
| 92 | 100 |
| Comparative chemical A | 50 |
| Comparative chemical B | 0 |
| Comparative chemical D | 55 |

Test Example 5: Ovicidal test for two-spotted spider mite (concentration: 20 ppm)

Female adults of two-spotted spider mite are placed on two leaf discs of kidney bean (diameter:10 mm) and oviposited over 24 hours, and thereafter these adults are removed therefrom. The wettable powder prepared according to Formulation Example 2 is diluted with water so that the concentration of the active ingredient is 20 ppm and sufficiently applied to these leaf discs. After the treatment, the leaf discs are placed in a thermostatic chamber of 25° C. for 7 days and then the number of unhatched eggs is counted to calculate the percentage of ovicidal activity. The test is carried out by double series. The results are shown in Table 13.

TABLE 13

| Compound No. | Ovicidal activity (%) |
|---|---|
| 98 | 100 |
| 99 | 100 |
| 100 | 100 |
| 101 | 100 |
| 107 | 100 |
| Comparative chemical A | 65 |
| Comparative chemical B | 20 |
| Comparative chemical C | 70 |
| Comparative chemical D | 36 |

Test Example 6: Control test for two-spotted spider mite

The wettable powder prepared according to Formulation Example 2 is diluted with water so that the concentration of the active ingredient is 500 ppm. In the resulting diluted wettable powder are immersed soy bean seedlings previously inoculated with 30–40 adults of two-spotted spider mite and then dried in air. After the treatment, the soy bean seedlings are placed in a thermostatic chamber of 25° C. for 14 days and then the number of living adults is counted to calculate the percentage of control efficiency according to the following calculation formula. The test is carried out by double series. The results are shown in Table 14.

Control efficiency (%)=[1—(number of adults before treatment at non-treated spot x number of adults after 14 days at treated spot)/(number of adults before treatment at treated spot x number of adults after 14 days at non-treated spot)]×100

TABLE 14

| Compound No. | Control efficiency (%) |
|---|---|
| 95 | 100 |
| 98 | 95 |
| 99 | 100 |
| 101 | 100 |
| 107 | 100 |
| 113 | 100 |
| Comparative chemical A | 65 |
| Comparative chemical B | 0 |
| Comparative chemical D | 0 |

Test Example 7: Ovicidal test for citrus red mite

Female adults of citrus red mite are placed on two laminae of citrus fruit (diameter: 10 mm) and oviposited over 2 days, and thereafter these adults are removed therefrom. The wettable powder prepared according to Formulation Example 2 is diluted with water so that the concentration of the active ingredient is 100 ppm, and the laminae are immersed therein for 10 seconds. After the treatment, the laminae are placed in a thermostatic chamber of 25° C. for 7 days and then the number of unhatched eggs is counted to calculate the percentage of ovicidal activity. The test is carried out by double series. The results are shown in Table 15.

TABLE 15

| Compound No. | Ovicidal activity (%) |
|---|---|
| 25 | 100 |
| 40 | 100 |
| 49 | 100 |
| 50 | 100 |
| 51 | 100 |
| 57 | 100 |
| 67 | 100 |
| 68 | 100 |
| 69 | 100 |
| 71 | 100 |
| 72 | 100 |
| 72 | 100 |
| 73 | 100 |
| 74 | 100 |
| 75 | 100 |
| 76 | 100 |
| 77 | 100 |
| 78 | 100 |
| Comparative chemical A | 20 |
| Comparative chemical B | 40 |
| Comparative chemical D | 45 |

Test Example 8: Insecticidal test for diamond-back moth

The wettable powder prepared according to Formulation Example 2 is diluted with water so that the concentration of the active ingredient is 500 ppm. Cabbage leaves are immersed in the resulting diluted solution, dried in air and then placed in a vinyl chloride cup. Ten larvae of diamond-back moth are released in the cup and thereafter a cover is placed thereon. Then, the cup is placed in a thermostatic chamber of 25° C. for 6 days, and the number of larvae died is counted to calculate the percentage of mortality. The test is carried out by double series. The results are shown in Table 16.

TABLE 16

| Compound No. | Mortality (%) |
|---|---|
| 2 | 100 |
| 6 | 100 |
| 9 | 100 |
| 10 | 100 |
| 11 | 100 |
| 12 | 100 |
| 14 | 100 |
| 21 | 100 |
| 22 | 100 |
| 25 | 100 |
| 28 | 95 |
| 40 | 100 |
| 42 | 100 |
| 56 | 100 |
| 57 | 100 |
| 66 | 90 |
| Comparative chemical A | 5 |
| Comparative chemical B | 50 |
| Comparative chemical C | 20 |

Test Example 9: Test for the preventive control of sheath blight

Paddy rice (variety: Kinnanpuu) is sowed on an unglazed pot of 7 cm in diameter in an amount of 15 seeds per pot and nursed in a greenhouse for 4–5 weeks. The wettable powder prepared according to Formulation Example 2 is diluted with water so that the concentration of the active ingredient is 500 ppm and sprayed on the rice seedling with fifth developed leaves in an amount of 10 ml per pot. After the drying in air, sheath blight (Rhizoctonia solani) cultured on hull medium is inoculated on the rootstock of the rice, which is immediately placed in a greenhouse of 28° C. After 6 days, the height of lesion formed in a coleoptile portion of the rice is measured to calculate the percentage of control value according to the following calculation formula. The results are shown in Table 17.

TABLE 17

Control value (%) = (1 - lesion height in treated area/ lesion height in non-treated area) × 100

| Compound No. | Control value (%) |
|---|---|
| 95 | 92 |
| 97 | 80 |
| 100 | 95 |
| 106 | 87 |
| 107 | 100 |
| Comparative chemical A | 73 |
| Comparative chemical C | 51 |
| Non-treated | 0 |

We claim:

1. A triazole derivative represented by a general formula:

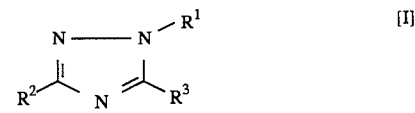

wherein $R^1$ is an alkyl (C1-C4) group, $R^2$ is a phenyl group which may be substituted with a halogen atom, an alkyl (C1-C4) group, an alkoxy (C1-C4) group, a nitro group, a cyano group or a trifluoromethyl group (these substituents in the phenyl group may be 1–5, and a combination thereof may be same or different), and $R^3$ is an alkenyl (C3-C15) group substituted with 1–4 halogen atoms.

2. A triazole derivative according to claim 1, wherein $R^1$ is methyl group or ethyl group, $R^2$ is a phenyl group which may be substituted with a halogen atom, a straight or branched alkyl (C1-C3) group, a methoxy group, a nitro group, a cyano group or a trifluoromethyl group (these substituents in the phenyl group may be 1–5, and a combination thereof may be same or different), and $R^3$ is 2-chloro-1-alkenyl (C3-C15) group or 2-bromo-1-alkenyl (C3-C15) group.

3. An insecticidal and acaricidal composition comprising an insecticidally and acaricidally effective amount of a triazole derivative as defined in claim 1 and a diluting agent.

4. A method of controlling harmful pests by applying an insecticidally and acaricidally effective amount of a triazole derivative as defined in claim 1 to positions infected by insects, mites or a combination thereof.

* * * * *